US009558545B2

(12) United States Patent
Vukkadala et al.

(10) Patent No.: US 9,558,545 B2
(45) Date of Patent: Jan. 31, 2017

(54) PREDICTING AND CONTROLLING CRITICAL DIMENSION ISSUES AND PATTERN DEFECTIVITY IN WAFERS USING INTERFEROMETRY

(71) Applicant: KLA-Tencor Corporation, Milpitas, CA (US)

(72) Inventors: Pradeep Vukkadala, Fremont, CA (US); Sathish Veeraraghavan, Santa Clara, CA (US); Soham Dey, Fremont, CA (US); Jaydeep Sinha, Livermore, CA (US)

(73) Assignee: KLA-Tencor Corporation, Milpitas, CA (US)

(*) Notice: Subject to any disclaimer, the term of this patent is extended or adjusted under 35 U.S.C. 154(b) by 53 days.

(21) Appl. No.: 14/730,997

(22) Filed: Jun. 4, 2015

(65) Prior Publication Data

US 2016/0163033 A1 Jun. 9, 2016

Related U.S. Application Data

(60) Provisional application No. 62/087,194, filed on Dec. 3, 2014.

(51) Int. Cl.
| | | |
|---|---|---|
| *G06K 9/00* | (2006.01) | |
| *G06T 7/00* | (2006.01) | |
| *G06K 9/62* | (2006.01) | |
| *G06F 17/50* | (2006.01) | |

(52) U.S. Cl.
CPC ........... *G06T 7/0004* (2013.01); *G06K 9/6201* (2013.01); *G06T 7/001* (2013.01); *G06T 2207/10004* (2013.01); *G06T 2207/30148* (2013.01)

(58) Field of Classification Search
CPC .............. G06K 9/00; G06T 7/00; G01N 21/00
USPC .............................................. 382/145; 716/55
See application file for complete search history.

(56) References Cited

U.S. PATENT DOCUMENTS

| 8,572,517 B2 * | 10/2013 | Pramanik et al. ...... G03F 1/144 |
| | | 716/50 |
| 2010/0208978 A1 | 8/2010 | Terasawa et al. |
| 2014/0145192 A1 | 5/2014 | Momono |

FOREIGN PATENT DOCUMENTS

| JP | 2004-343060 A1 | 12/2004 |
| JP | 2008-076377 A | 4/2008 |
| JP | 2011-013227 A1 | 1/2011 |

OTHER PUBLICATIONS

PCT Search Report for PCT/US2015/063032 dated Mar. 31, 2016.

* cited by examiner

*Primary Examiner* — Abolfazl Tabatabai
(74) *Attorney, Agent, or Firm* — Suiter Swantz pc llo

(57) ABSTRACT

Systems and methods for predicting and controlling pattern quality data (e.g., critical dimension and/or pattern defectivity) in patterned wafers using patterned wafer geometry (PWG) measurements are disclosed. Correlations between PWG measurements and pattern quality data measurements may be established, and the established correlations may be utilized to provide pattern quality data predictions for a given wafer based on geometry measurements obtained for the give wafer. The predictions produced may be provided to a lithography tool, which may utilize the predictions to correct focus and/or title errors that may occur during the lithography process.

22 Claims, 7 Drawing Sheets

PREDICTING AND CONTROLLING CRITICAL DIMENSION ISSUES AND PATTERN DEFECTIVITY IN WAFERS USING INTERFEROMETRY

CROSS-REFERENCE TO RELATED APPLICATIONS

The present application claims the benefit under 35 U.S.C. §119(e) of U.S. Provisional Application Ser. No. 62/087,194, filed Dec. 3, 2014. Said U.S. Provisional Application Ser. No. 62/087,194 is hereby incorporated by reference in its entirety.

TECHNICAL FIELD

The disclosure generally relates to the field of semiconductor fabrication, and particularly to prediction and control of critical dimension and pattern defectivity during semiconductor fabrication.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Wafers are typically patterned during the fabrication process. Lithography, for example, is a semiconductor fabrication process that involves transferring a pattern from a reticle to a resist arranged on a semiconductor wafer. The performance of a lithography process may be evaluated at least partially based on the minimum feature size (i.e., critical dimension, or CD) and/or the presence of any defective patterns (i.e., pattern defectivity).

It is noted that critical dimension and pattern defectivity observed in silicon wafers are typically affected by focus errors (i.e., defocus) that may occur during patterning in a lithography process. It is also noted that the geometry of a wafer (i.e., wafer geometry) is a factor that may lead to focus errors during lithography. Therein lies a need for systems and methods to help improve critical dimension and pattern defectivity during semiconductor fabrication by taking wafer geometry into consideration.

SUMMARY

An embodiment of the present disclosure is directed to a method. The method may include: obtaining pattern quality data for at least one reference wafer; generating at least one pattern quality binary map for the at least one reference wafer; obtaining patterned wafer geometry data for the at least one reference wafer; generating at least one patterned wafer geometry binary map for the at least one reference wafer based on at least one threshold; selecting a threshold among the at least one threshold, the selected threshold providing a best matching between the at least one patterned wafer geometry binary map and the at least one pattern quality binary map; and providing a pattern quality data prediction for a new wafer based on the selected threshold.

A further embodiment of the present disclosure is directed to a system. The system may include one or more imaging device configured to obtain pattern quality data and patterned wafer geometry data for at least one reference wafer. The system may also include a processor in communication with the one or more imaging device. The processor may be configured to: generate at least one pattern quality binary map for the at least one reference wafer; generate at least one patterned wafer geometry binary map for the at least one reference wafer based on at least one threshold; select a threshold among the at least one threshold, wherein the selected threshold provides a best matching between the at least one patterned wafer geometry binary map and the at least one pattern quality binary map; and provide a pattern quality data prediction for a new wafer based on the selected threshold.

Another embodiment of the present disclosure is directed to a method for providing critical dimension predictions. The method may include: obtaining critical dimension measurements for a reference wafer at a plurality of critical dimension measurement sites; generating a critical dimension binary map for the reference wafer, wherein the a critical dimension binary map indicates whether the critical dimension within the plurality of critical dimension measurement sites is acceptable or unacceptable; obtaining patterned wafer geometry measurements for the reference wafer at a plurality of patterned wafer geometry measurement sites; generating at least one patterned wafer geometry binary map for the reference wafer based on at least one threshold; selecting a threshold among the at least one threshold responsible for generating a best matching patterned wafer geometry binary map against the critical dimension binary map; and providing a critical dimension prediction for a new wafer based on the selected threshold.

An additional embodiment of the present disclosure is directed to a method for providing pattern defect predictions. The method may include: obtaining pattern defect measurements for a reference wafer at a plurality of pattern defect measurement sites; generating a pattern defect binary map for the reference wafer, wherein the a pattern defect binary map indicates whether the pattern defect measurement within the plurality of pattern defect measurement sites is acceptable or unacceptable; obtaining patterned wafer geometry measurements for the reference wafer at a plurality of patterned wafer geometry measurement sites; generating at least one patterned wafer geometry binary map for the reference wafer based on at least one threshold; selecting a threshold among the at least one threshold responsible for generating a best matching patterned wafer geometry binary map against the pattern defect binary map; and providing a pattern defect prediction for a new wafer based on the selected threshold.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Wafer metrology systems capable of measuring patterned wafers may be referred to as patterned wafer geometry (PWG) measurement systems. Interferometer wafer metrology systems, such as WaferSight metrology systems from KLA-Tencor, are exemplary PWG measurement systems. Such systems may use imaging devices (e.g., double-Fizeau interferometry imaging devices) to make high resolution (e.g., 125 um-500 um pixel width) surface height measurements of front and/or back surfaces of patterned wafers. Various PWG measurements may be obtained and/or derived using PWG measurement systems. Such PWG measurements may include wafer frontside height, backside height, thickness variation, flatness, and all consequent derivatives such as shape, nanotopography and the like.

Embodiments in accordance with the present disclosure are directed to systems and methods for predicting and controlling critical dimension and/or pattern defectivity in patterned wafers using patterned wafer geometry (PWG) measurements. Correlations between PWG measurements and critical dimension measurements may be established, and the established correlations may be utilized to predict critical dimension values for a given wafer based on geometry measurements obtained for the give wafer. Similarly, correlations between PWG measurements and pattern defects may be established, and the established correlations may be utilized to predict pattern defectivity for a given wafer based on geometry measurements obtained for the give wafer. The predicted critical dimension values and/or pattern defectivity may then be utilized as control information to help improve a fabrication process (e.g., to mitigate defocus during lithography) for the given wafer.

Figure 1:
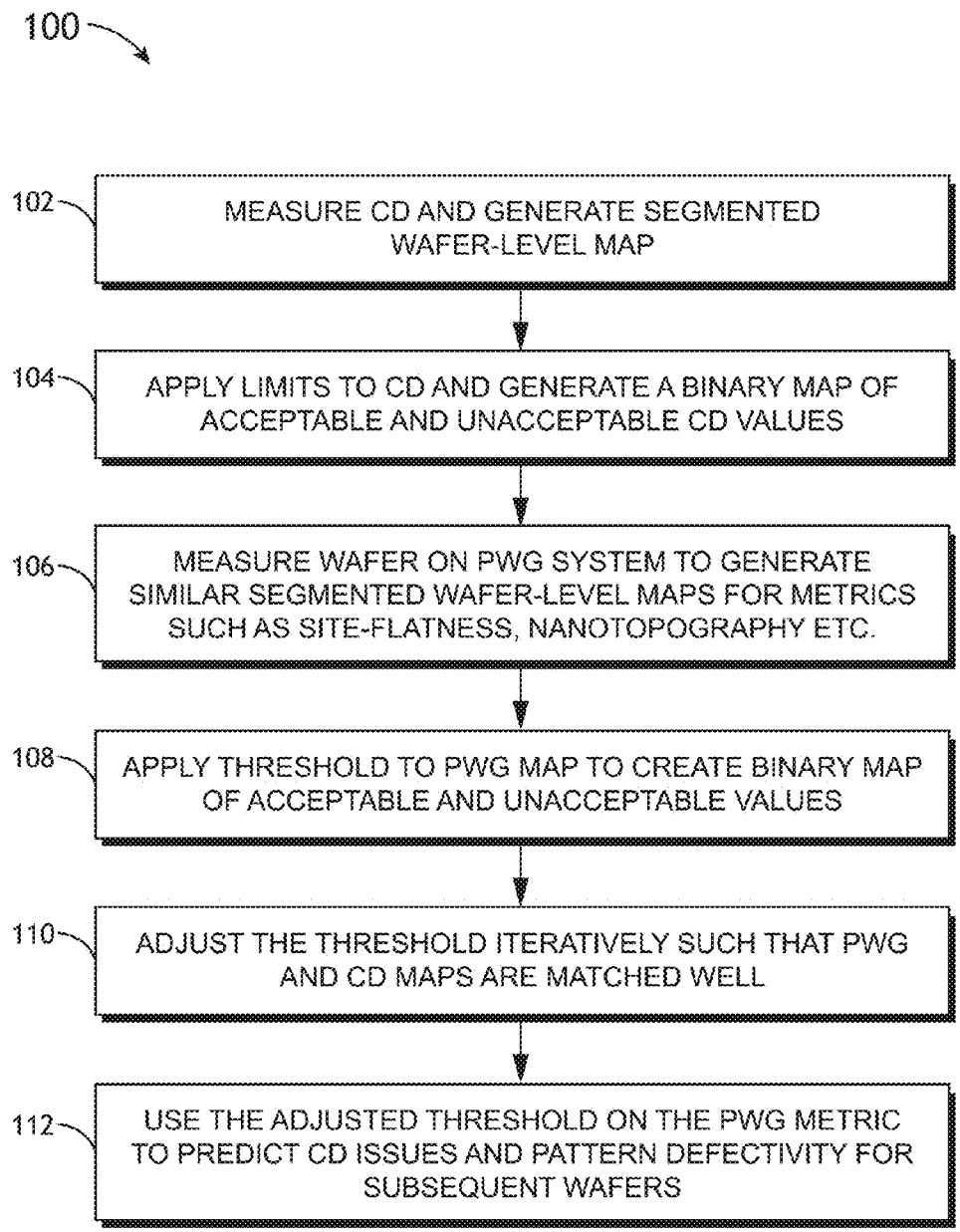
FIG. 1 is a flow diagram depicting an embodiment of a method for establishing a correlation between patterned wafer geometry measurements and critical dimension measurements.
Figure 2:
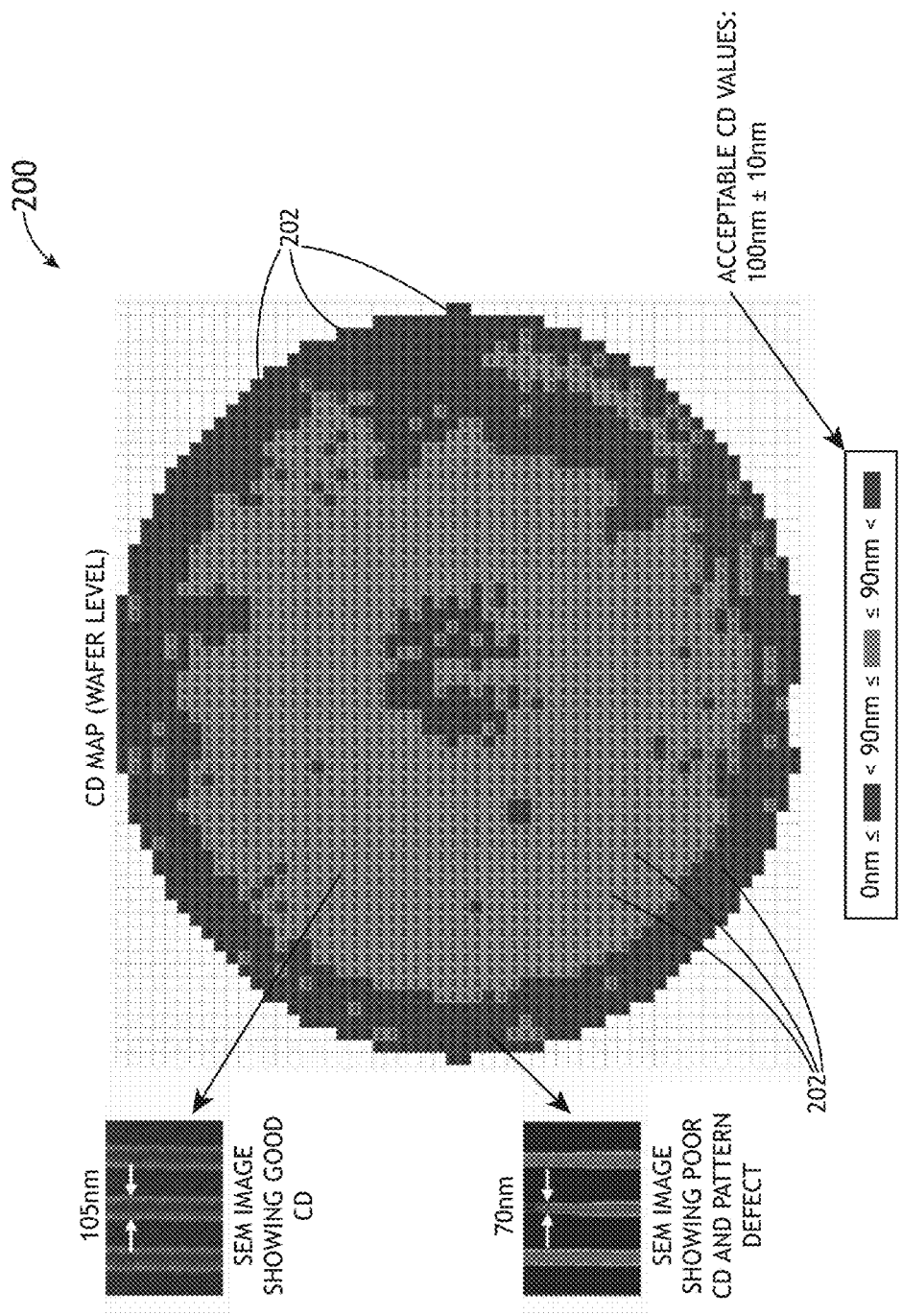
FIG. 2 is an illustration depicting segmentation of a wafer and a wafer-level critical dimension binary map.
Figure 3:
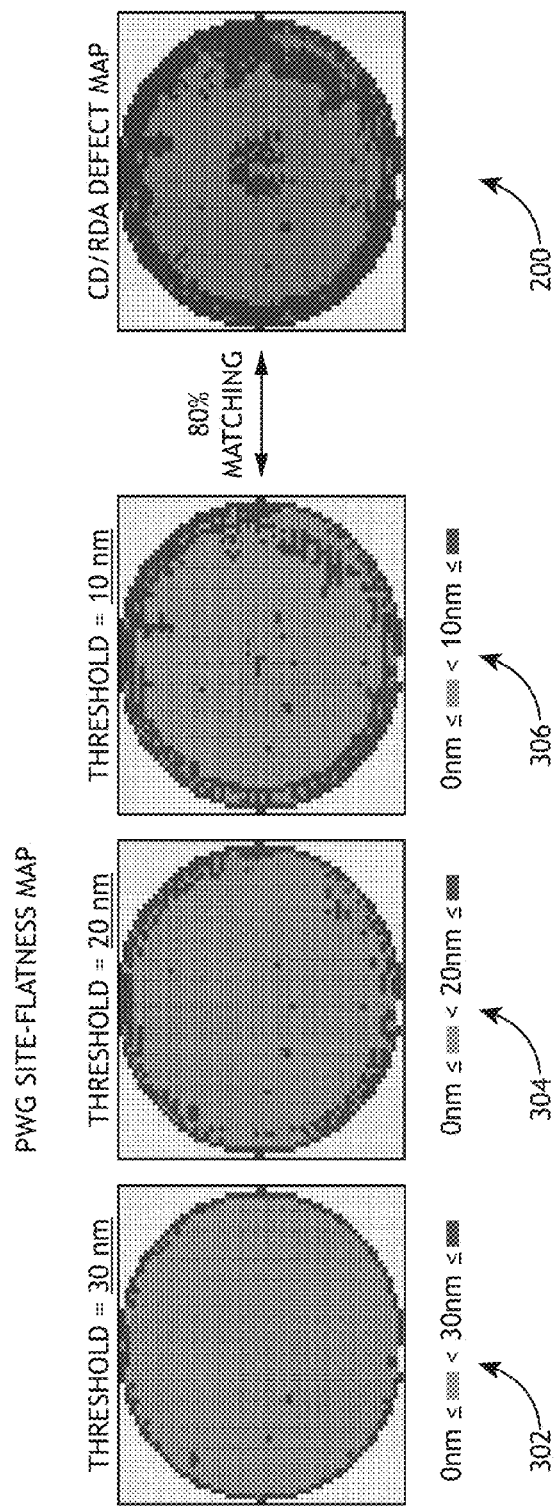
FIG. 3 is an illustration depicting a threshold selection process for selecting a threshold that provides a best matching wafer-level patterned wafer geometry binary map against a wafer-level critical dimension binary map.

Referring generally to FIGS. 1-3. FIG. 1 is a flow diagram depicting an embodiment of a method 100 for establishing a correlation between PWG measurements and critical dimension measurements. Critical dimension measurements may be measured for one or more reference wafers in step 102. The reference wafers may have been processed utilizing the same process tool(s). Analyzing these reference wafers may help establishing the correlation between PWG measurements and critical dimension measurements, and the established correlation may be utilized to predict critical dimension values for a subsequent wafer that is going to be processed by the same process tool(s).

As shown in FIG. 2, a wafer 200 being measured in step 102 may be segmented into a plurality of measurement sites 202, and a critical dimension measurement may be obtained for each of the measurement sites 202. It is contemplated that the critical dimension measurement for each measurement site 202 may be obtained by taking a measurement of the critical dimension at a single point within that measurement site 202. Alternatively and/or additionally, multiple measurements may be taken at multiple points within a particular measurement site 202, and a statistical representation (e.g., an average, a minimum, or a maximum value) of the multiple measurements taken within the particular measurement site 202 may be utilized as the critical dimension measurement for that particular measurement site 202.

It is to be understood that the granularity of the measurement sites 202 shown in FIG. 2 is exemplary. The measurement sites 202 may be segmented more coarsely or more finely without departing from the spirit and scope of the present disclosure. It is also to be understood that it may not be necessary to obtain critical dimension measurement for every measurement site 202 defined within the wafer 200 (e.g., critical dimension measurements may be taken for only a subset of the defined measurement sites 202). While the particular sites where critical dimension measurements are taken may vary, it may be beneficial to obtain critical dimension measurements for those measurement sites 202 near the edges of the wafer 200, where patterning issues may be prevalent.

Once the critical dimension measurements are obtained for at least a subset of the measurement sites 202 defined within the wafer 200, a wafer-level critical dimension map may be generated accordingly in step 104. In some embodiments, predefined upper and lower limits may be utilized to determine whether a measured critical dimension is acceptable (e.g., within the limits) or unacceptable (e.g., outside the limits). By comparing the critical dimension measurements against the predefined upper and lower limits, a wafer-level critical dimension binary map (i.e., acceptable or unacceptable) may be generated.

FIG. 2 represents an exemplary depiction of such a wafer-level critical dimension binary map, wherein the shaded measurement sites have been deemed unacceptable. It is to be understood, however, that such a depiction is merely exemplary; a wafer-level critical dimension binary map in accordance with the present disclosure may be presented in various other manners without departing from the spirit and scope of the present disclosure. It is also to be understood that a graphical representation of the wafer-level critical dimension binary map is not required. That is, the method steps described herein may utilize the information presented in these maps without requiring the maps to be displayed. The maps depicted herein are shown for illustrative purposes.

It is contemplated that in order to establish a correlation between patterned wafer geometry (PWG) and critical dimension, PWG measurements for the same set of one or more reference wafers may need to be obtained in step 106 in addition to the critical dimension measurements obtained in step 102. Similar to the critical dimension measurements, the PWG measurements may also be segmented into the plurality of measurement sites. Using wafer flatness as an example, instead of using a single flatness value to represent the flatness of an entire wafer, a site-specific flatness value may be obtained for each measurement site, and a plurality of site-specific flatness values obtained from a plurality of measurement sites may jointly form a site-based flatness map representing the flatness of the entire wafer. It is contemplated that while the measurement sites for critical dimension measurements may be segmented differently than the measurement sites for PWG measurements, they may also be segmented in substantially similar manners without departing from the spirit and scope of the present disclosure.

Also similar to the critical dimension measurements, the PWG measurements obtained in step 106 may be utilized to generate a wafer-level PWG binary map in step 108. Continue with the example above where a site-based flatness map is obtained, a flatness threshold may be applied to the site-based flatness map, and the measurement sites having a flatness value below the threshold may be deemed acceptable while the measurement sites having a flatness value equal to or greater than the threshold may be deemed unacceptable.

It is noted that the threshold utilized to in step 108 to generate the wafer-level PWG binary map is a variable that needs to be determined in step 110. As shown in FIG. 3, different threshold values may be utilized to generate different wafer-level PWG binary maps 302, 304, and 306, and the threshold value that produced the wafer-level PWG binary map that most closely matches with the wafer-level critical dimension binary map 200 may be identified as the threshold that can be used to make predictions. For illustrative purposes, threshold value 10 nm in the example depicted in FIG. 3 is capable of producing the wafer-level PWG binary map 306, which most closely matches with the wafer-level critical dimension binary map 200, and therefore threshold value 10 nm may be determined to be the threshold value that produces the best matching wafer-level PWG binary map against the wafer-level critical dimension binary map 200.

It is to be understood that while three threshold values are shown in the example depicted in FIG. 3, the number of threshold values taken into consideration may vary without departing from the spirit and scope of the present disclosure. It is also to be understood that the different threshold values may be considered iteratively, sequentially, and/or concurrently. It is to be understood that while the specific implementations may vary, the objective may remain the same, which is to identify a threshold value that produces the best matching wafer-level PWG binary map against the wafer-level critical dimension binary map 200.

It is also noted that if multiple reference wafers are being analyzed, PWG measurements of each reference wafer may be obtained and their wafer-level PWG binary maps may be compared with their corresponding wafer-level critical dimension binary maps. In such instances, a threshold value that optimizes the matching between the wafer-level PWG binary maps and their corresponding wafer-level critical dimension binary maps across all reference wafers may be identified as the threshold value. In order words, if multiple wafers are being analyzed, step 110 is configured to determine a threshold value that produces the best overall matching for the multiple wafers.

Once the threshold value is determined in step 110, this threshold value may be utilized in step 112 to help predict critical dimension issues and/or pattern defects that may be likely to occur for subsequent wafers. For instance, by taking PWG measurements (e.g., flatness, as described in the examples above) of a new wafer and generating a wafer-level PWG binary map for the new wafer based on the determined threshold and the measurements taken, the resulting map may closely resemble/predict a critical dimension or a pattern defects map of that new wafer.

To reiterate, PWG measurements may include wafer frontside height, backside height, thickness variation, flatness, and all consequent derivatives such as shape, nano-topography and the like. It is to be understood that while wafer flatness is utilized as an exemplary PWG measurement in the examples above, other PWG measurements may be utilized by the method 100 instead of or in conjunction with wafer flatness without departing from the spirit and scope of the present disclosure.

Figure 4:
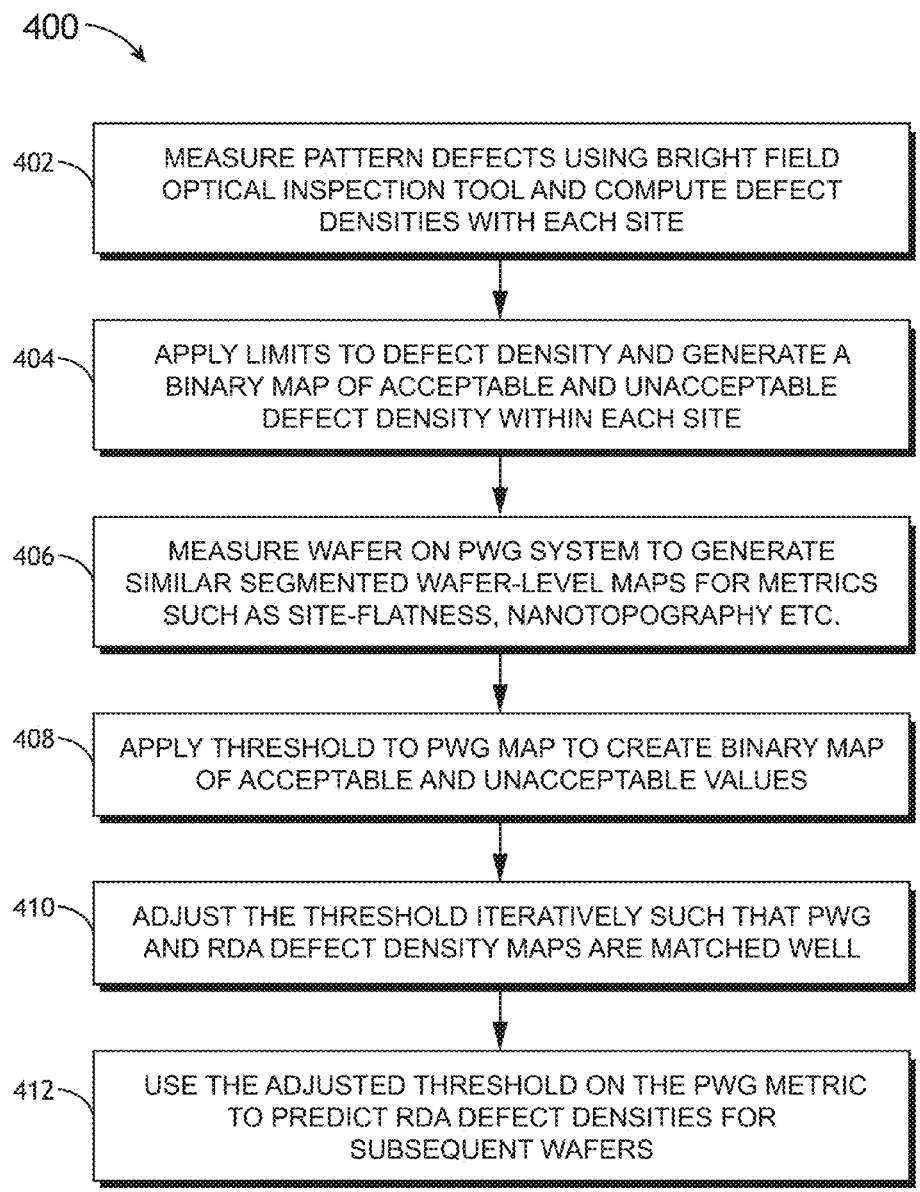
FIG. 4 is a flow diagram depicting an embodiment of a method for establishing a correlation between patterned wafer geometry measurements and pattern defect density measurements.

It is also contemplated that critical dimension is only one type of pattern quality data that can be correlated for prediction purposes. Other types of pattern quality data, such as pattern defects and defect densities, may also be correlated to PWG measurements and utilized to provide predictions. FIG. 4 is a flow diagram depicting an embodiment of a method 400 for establishing a correlation between PWG measurements and pattern defects.

Figure 5:
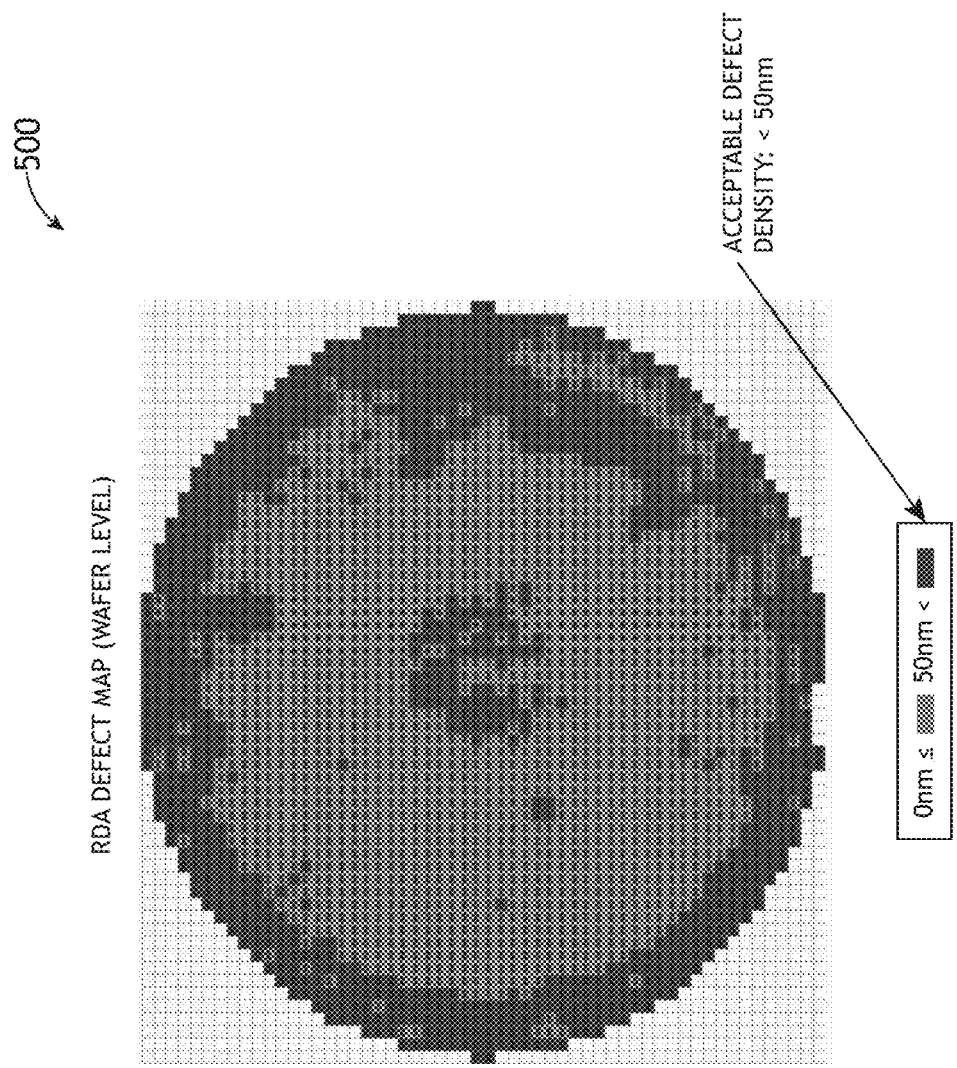
FIG. 5 is an illustration depicting segmentation of a wafer and a wafer-level defect density binary map.

As shown in FIG. 4, one or more inspection tools may be utilized to measure the pattern defects in step 402. For instance, bright field optical inspection may be performed at a given layer of the wafer to obtain the defect map along with spatial awareness of the defects. The defect map may then be segmented into multiple measurement sites as shown in FIG. 5, and a defect density value may be determined for at least some of the measurement sites. It is noted that while the particular sites where defect density values are determined may vary, it may be beneficial to determine defect density values for those measurement sites near the edges of the wafer, where patterning issues may be prevalent.

Similar to the process utilized to generate the wafer-level critical dimension binary map, a wafer-level defect density binary map 500 may be generated in step 404 based on the determined defect density values and a predefined defect density acceptance limit. More specifically, by comparing defect density values against the predefined defect density acceptance limit, measurement sites that are deemed acceptable (e.g., below the limit) and measurement sites that are deemed unacceptable (e.g., above the limit) may be identified.

It is contemplated that the method steps 406 through 412 may be performed in a similar manner as the method steps 106 through 112 previously described. That is, step 406 may obtain PWG measurements for the wafer(s) whose defect density values are being determined, step 408 may generate a wafer-level PWG binary map based on the PWG measurements obtained, step 410 may determine a threshold value that produces the best matching wafer-level PWG binary map against the wafer-level defect density binary map 500, and step 412 may then utilize the threshold value to help predict pattern defects and/or defect densities that may be likely to occur for subsequent wafers.

It is contemplated that providing the abilities to establish correlations directly between PWG measurements and pattern quality data (e.g., critical dimension, pattern defect measurements and the like), and the abilities to predict such pattern quality data based on PWG measurements, may be appreciated and may be utilized for various performance analysis and process control purposes. For instance, FIG. 6 shows a block diagram depicting a control process that may be utilize to improve focus (and in turn improve critical dimension and pattern defectivity of the wafer produced) using PWG measurements based prediction.

Figure 6:
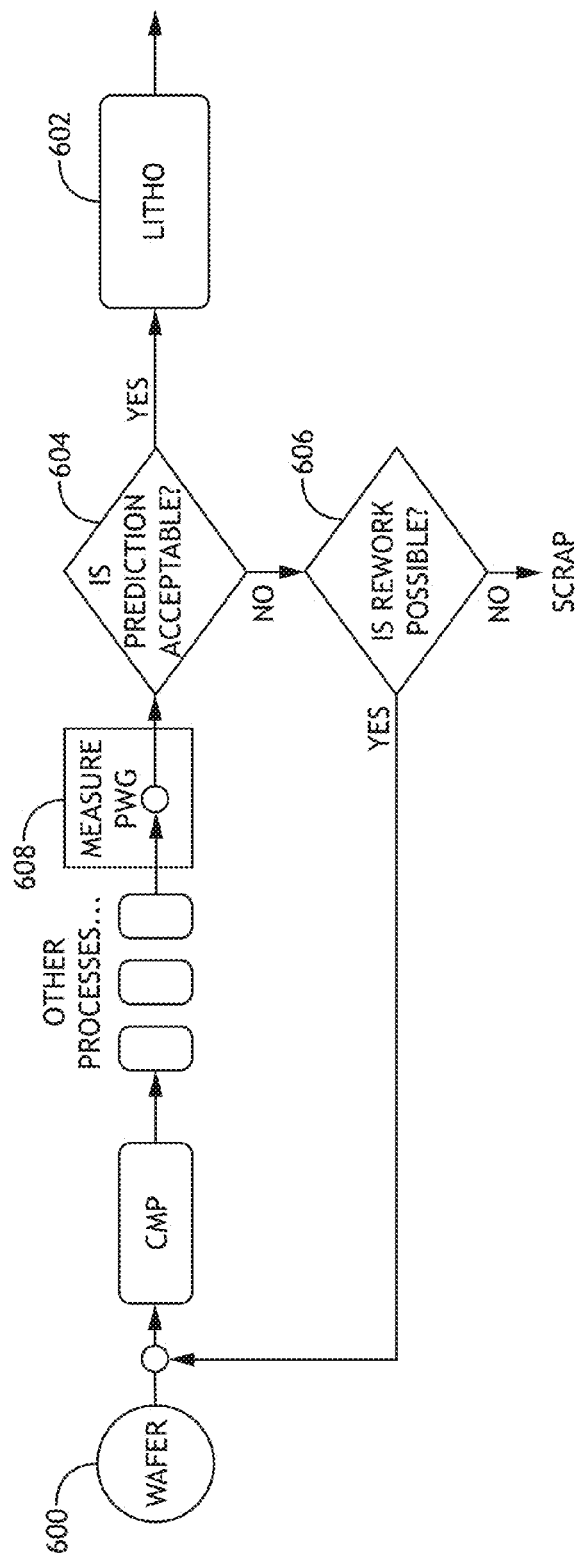
FIG. 6 is a block diagram depicting a control process utilizing patterned wafer geometry measurements based prediction.

More specifically, as shown in FIG. 6, PWG measurements of a wafer 600 may be taken prior to undergoing a lithography process 602, and a prediction system 608 may utilize the PWG measurements to predict critical dimension issues, pattern defects, and/or defect densities that may be observed on the wafer 600 if the wafer 600 undergo the lithography process 602. If the prediction (e.g., in terms of a predicted critical dimension map and/or a predicted defect densities map) result is determined (604) to be within an acceptable tolerance level, the wafer 600 may be allowed to proceed to the lithography process 602. Otherwise, the control process may determine (606) whether re-processing on the wafer 600 is feasible or possible. For example, if re-polishing the wafer 600 may help improve the wafer flatness, which may in turn improve the predicted critical dimension map for this wafer 600, a determination (606) may be made to re-process this wafer 600 in order to better prepare the wafer 600 for the lithography process 602. On the other hand, if it is determined that re-processing the wafer 600 is not feasible and/or is unlikely to better prepare the wafer 600 for the lithography process 602, the wafer 600 may be discarded without undergoing the lithography process 602.

Figure 7:
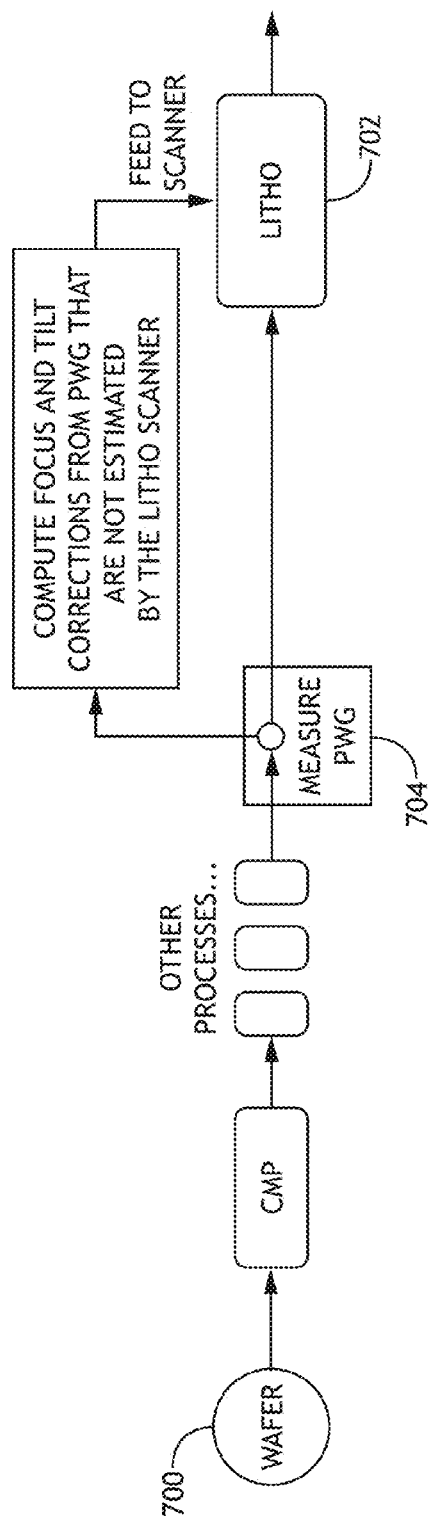
FIG. 7 is a block diagram depicting another control process utilizing patterned wafer geometry measurements based prediction.

FIG. 7 is a block diagram depicting another control process that may be utilize to improve focus (and in turn improve critical dimension and pattern defectivity of the wafer produced) using PWG measurements based prediction. As shown in FIG. 7, PWG measurements of a wafer 700 may be taken prior to undergoing a lithography process 702, and a prediction system 704 may utilize the PWG measurements to predict critical dimension issues, pattern defects, and/or defect densities that may be observed on the wafer 700. The predictions produced in this manner may then be provided to a lithography tool (e.g., a lithography scanner) used to carry out the lithography process 702, and the lithography tool may utilize the information provided by the prediction system 704 to improve computation of focus and tilt corrections/offsets in order to correct for focus and title errors that would otherwise be experienced by a new wafer during the lithography process.

It is noted that existing lithography scanners typically compute focus and tilt corrections (referred to as focus correctables and tilt correctables) for each exposure slit based on scanner leveling measurement data and adjust the scanner stage to print pattern structures at estimated best focus settings. However, their abilities are limited due to issues such as reduced sampling of scanner leveling system and inaccuracies associated with measurement of transparent films which is highly prevalent in silicon wafer processing. These issues are exacerbated especially at the near-edge regions of the wafer. It is therefore contemplated that providing additional focus and tilt corrections generated based on PWG measurements, specifically the corrections for the measurement sites that are predicted to be unacceptable (e.g., predicted to be outside of the acceptable limits for critical dimension, pattern defects, and/or defect densities), may improve the overall effectiveness of the focus and tilt corrections utilized by the lithography scanners, which may in turn improve critical dimension and pattern defectivity of the wafers produced.

It is contemplated that various techniques may be utilized to generate the additional focus and/or tilt correctables based on PWG measurements. For example, flatness measurements obtained from a PWG measurement tool may be utilized in conjunction with scanner leveling metrology data to compute the focus and tilt corrections. More specifically, a flatness difference map may be computed based on the differences between the wafer flatness data obtained from the PWG measurement tool and the wafer flatness data obtained from the scanner. The difference map may then be divided into exposure slits, and the focus and tilt corrections may be calculated for each exposure slit that contains one or more measurement sites that are predicted to be unacceptable. Alternatively and/or additionally, the difference map may be obtained using flatness measurements of a wafer pre-opaque film coating and post-opaque film coating. In addition, it is contemplated that focus and tilt offsets may be calculated solely from measurements obtained from the PWG total without using scanner leveling measurement system. It is contemplated that other techniques may be utilized to generate the additional focus and tilt corrections without departing from the spirit and scope of the present disclosure.

It is contemplated that the prediction systems in accordance with the present disclosure may include a processor configured to execute one or more prediction methods described above. The processor may be implemented as a dedicated processing unit, an application-specific integrated circuit (ASIC), an integrated component of an existing hardware, firmware or software configured to control operations of one or more process and/or wafer geometry measurement tools, or various other types of processing units without departing from the spirit and scope of the present disclosure.

It is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A method, comprising:
   obtaining pattern quality data for at least one reference wafer;
   generating at least one pattern quality binary map for the at least one reference wafer;
   obtaining patterned wafer geometry data for the at least one reference wafer;
   generating at least one patterned wafer geometry binary map for the at least one reference wafer based on at least one threshold;
   selecting a threshold among the at least one threshold, the selected threshold providing a best matching between the at least one patterned wafer geometry binary map and the at least one pattern quality binary map; and
   providing a pattern quality data prediction for a new wafer based on the selected threshold.

2. The method of claim 1, wherein said providing a pattern quality data prediction for a new wafer based on the selected threshold further comprises:
   obtaining patterned wafer geometry data for the new wafer;
   generating a patterned wafer geometry binary map for the new wafer based on the selected threshold; and
   providing a predicted pattern quality binary map for the new wafer based on the patterned wafer geometry binary map.

3. The method of claim 1, wherein the pattern quality data includes at least one of: a critical dimension measurement and a pattern defect measurement.

4. The method of claim 1, wherein said generating at least one pattern quality binary map for the at least one reference wafer further comprises:
dividing the at least one reference wafer into a plurality of pattern quality measurement sites; and
indicating whether the pattern quality data within the plurality of pattern quality measurement sites is acceptable or unacceptable.

5. The method of claim 4, wherein said generating at least one patterned wafer geometry binary map for the at least one reference wafer based on at least one threshold further comprises:
dividing the at least one reference wafer into a plurality of patterned wafer geometry measurement sites; and
indicating whether the pattern quality data within the plurality of measurement sites is below or above the at least one threshold.

6. The method of claim 5, wherein the plurality of pattern quality measurement sites and the plurality of patterned wafer geometry measurement sites are substantially similar.

7. The method of claim 1, wherein the pattern quality data prediction for the new wafer is provided prior to the new wafer undergoing a lithography process.

8. The method of claim 7, further comprising:
preventing the new wafer from entering the lithography process when the pattern quality data prediction for the new wafer is predicted to be unacceptable.

9. The method of claim 7, further comprising:
calculating at least one of a focus correctable and a tilt correctable for the new wafer; and
providing the at least one of a focus correctable and a tilt correctable to the lithography process for correction of at least one of a focus error and a title error during the lithography process.

10. A system, the system comprising:
an imaging device configured to obtain pattern quality data and patterned wafer geometry data for at least one reference wafer; and
a processor in communication with the imaging device, the processor configured to:
generate at least one pattern quality binary map for the at least one reference wafer;
generate at least one patterned wafer geometry binary map for the at least one reference wafer based on at least one threshold;
select a threshold among the at least one threshold, wherein the selected threshold provides a best matching between the at least one patterned wafer geometry binary map and the at least one pattern quality binary map; and
provide a pattern quality data prediction for a new wafer based on the selected threshold.

11. The system of claim 10, wherein the imaging device is further configured obtain patterned wafer geometry data for the new wafer, and wherein the processor is further configured to generate a patterned wafer geometry binary map for the new wafer based on the selected threshold and provide a predicted pattern quality binary map for the new wafer based on the patterned wafer geometry binary map.

12. The system of claim 10, wherein the pattern quality data includes at least one of: a critical dimension measurement and a pattern defect measurement.

13. The system of claim 10, wherein the processor generates the at least one pattern quality binary map for the at least one reference wafer by dividing the at least one reference wafer into a plurality of pattern quality measurement sites and indicating whether the pattern quality data within the plurality of pattern quality measurement sites is acceptable or unacceptable.

14. The system of claim 13, wherein the processor generates the at least one patterned wafer geometry binary map for the at least one reference wafer by dividing the at least one reference wafer into a plurality of patterned wafer geometry measurement sites and indicating whether the pattern quality data within the plurality of measurement sites is below or above the at least one threshold.

15. The system of claim 14, wherein the plurality of pattern quality measurement sites and the plurality of patterned wafer geometry measurement sites are substantially similar.

16. The system of claim 10, wherein the processor provides the pattern quality data prediction for the new wafer prior to the new wafer undergoing a lithography process.

17. The system of claim 16, wherein the processor is further configured to prevent the new wafer from entering the lithography process when the pattern quality data prediction for the new wafer is predicted to be unacceptable.

18. The system of claim 16, wherein the processor is further configured to calculate at least one of a focus correctable and a tilt correctable for the new wafer, and provide the at least one of a focus correctable and a tilt correctable to the lithography process for correction of at least one of a focus error and a title error during the lithography process.

19. A method, comprising:
obtaining critical dimension measurements for a reference wafer at a plurality of critical dimension measurement sites;
generating a critical dimension binary map for the reference wafer, wherein the a critical dimension binary map indicates whether the critical dimension within the plurality of critical dimension measurement sites is acceptable or unacceptable;
obtaining patterned wafer geometry measurements for the reference wafer at a plurality of patterned wafer geometry measurement sites;
generating at least one patterned wafer geometry binary map for the reference wafer based on at least one threshold;
selecting a threshold among the at least one threshold responsible for generating a best matching patterned wafer geometry binary map against the critical dimension binary map; and
providing a critical dimension prediction for a new wafer based on the selected threshold.

20. The method of claim 19, wherein said providing a critical dimension prediction for a new wafer based on the selected threshold further comprises:
obtaining patterned wafer geometry data for the new wafer;
generating a patterned wafer geometry binary map for the new wafer based on the selected threshold; and
providing a predicted critical dimension binary map for the new wafer based on the patterned wafer geometry binary map.

21. A method, comprising:
obtaining pattern defect measurements for a reference wafer at a plurality of pattern defect measurement sites;
generating a pattern defect binary map for the reference wafer, wherein the a pattern defect binary map indicates whether the pattern defect measurement within the plurality of pattern defect measurement sites is acceptable or unacceptable;

obtaining patterned wafer geometry measurements for the reference wafer at a plurality of patterned wafer geometry measurement sites;

generating at least one patterned wafer geometry binary map for the reference wafer based on at least one threshold;

selecting a threshold among the at least one threshold responsible for generating a best matching patterned wafer geometry binary map against the pattern defect binary map; and providing a pattern defect prediction for a new wafer based on the selected threshold.

22. The method of claim 21, wherein said providing a pattern defect prediction for a new wafer based on the selected threshold further comprises:

obtaining patterned wafer geometry data for the new wafer;

generating a patterned wafer geometry binary map for the new wafer based on the selected threshold; and providing a predicted pattern defect binary map for the new wafer based on the patterned wafer geometry binary map.

\* \* \* \* \*